US011246705B2

(12) United States Patent
Kizuka

(10) Patent No.: US 11,246,705 B2
(45) Date of Patent: Feb. 15, 2022

(54) SYSTEM AND METHOD FOR IMPLANT DELIVERY

(71) Applicant: ABBOTT CARDIOVASCULAR SYSTEMS INC., Santa Clara, CA (US)

(72) Inventor: Koji J. Kizuka, San Francisco, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 285 days.

(21) Appl. No.: 16/393,299

(22) Filed: Apr. 24, 2019

(65) Prior Publication Data

US 2019/0247187 A1    Aug. 15, 2019

Related U.S. Application Data

(63) Continuation of application No. 15/040,587, filed on Feb. 10, 2016, now Pat. No. 10,299,924.

(51) Int. Cl.
*A61F 2/24* (2006.01)
*A61F 2/95* (2013.01)

(52) U.S. Cl.
CPC .......... *A61F 2/2427* (2013.01); *A61F 2/2436* (2013.01); *A61F 2/2466* (2013.01); *A61F 2/95* (2013.01); *A61F 2210/0057* (2013.01)

(58) Field of Classification Search
CPC ........ A61F 2/2427; A61F 2/2466; A61F 2/95; A61B 1/08; A61B 1/0051; A61B 1/0055; A61B 1/0056; A61B 2017/003; A61M 25/0105; A61M 25/0133; A61M 25/0147
See application file for complete search history.

(56) References Cited

U.S. PATENT DOCUMENTS

| 5,042,707 | A  | * | 8/1991  | Taheri .................. A61B 17/115 606/213 |
| 8,052,607 | B2 |   | 11/2011 | Byrd |
| 8,721,591 | B2 |   | 5/2014  | Chang et al. |
| 8,852,112 | B2 |   | 10/2014 | Bielewicz et al. |
| 2004/0044350 | A1 | * | 3/2004 | Martin ................. A61B 1/0057 606/139 |

(Continued)

FOREIGN PATENT DOCUMENTS

WO    WO 2016/176610 A1    11/2016

OTHER PUBLICATIONS

U.S. Appl. No. 15/040,587 (U.S. Pat. No. 10,299,924), filed Feb. 10, 2016 (May 28, 2019).

(Continued)

*Primary Examiner* — Melanie R Tyson
(74) *Attorney, Agent, or Firm* — Baker Botts L.L.P.

(57) ABSTRACT

A method for delivering an implant including, a catheter having a shaft defined by a proximal end and a distal end and a bore extending therethrough; a first joint in the shaft, and a second joint in the shaft located distal of the first joint. The first joint and the second joint are separated by a first digit sized to receive the implant and located between the first joint and the second joint. The second joint and the distal end are separated by a second digit being sized to receive the implant. The implant is advanced through the first digit and into the second digit without bending the implant or the first and second digits by rotating the digits at the first joint and the second joint.

18 Claims, 14 Drawing Sheets

(56) References Cited

U.S. PATENT DOCUMENTS

| | | |
|---|---|---|
| 2007/0078504 A1* | 4/2007 | Mialhe ............... A61B 17/3439 623/1.11 |
| 2008/0051703 A1 | 2/2008 | Thornton et al. |
| 2009/0099554 A1 | 4/2009 | Forster et al. |
| 2012/0136350 A1 | 5/2012 | Goshgarian et al. |
| 2014/0135685 A1 | 5/2014 | Kabe et al. |

OTHER PUBLICATIONS

U.S. Appl. No. 15/040,587, Apr. 4, 2018 Restriction Requirement.
U.S. Appl. No. 15/040,587, May 31, 2018 Response to Restriction Requirement.
U.S. Appl. No. 15/040,587, Jul. 9, 2018 Non-final Office Action.
U.S. Appl. No. 15/040,587, Dec. 5, 2018 Response to Non-final Office Action.
U.S. Appl. No. 15/040,587, Jan. 18, 2019 Notice of Allowance.
U.S. Appl. No. 15/040,587, Apr. 16, 2019 Issue Fee Payment.
International Search Report and Written Opinion dated Apr. 10, 2017 in International Application No. PCT/US2017/016781, 11 pages.

* cited by examiner

SYSTEM AND METHOD FOR IMPLANT DELIVERY

CLAIM OF PRIORITY

The present application is a continuation of U.S. patent application Ser. No. 15/040,587 filed on Feb. 10, 2016, the content of which is incorporated by reference herein.

BACKGROUND

This application relates to systems and methods for implanting devices such as replacement heart valves, clips, stents, and similar repair devices within the anatomy of a patient.

It is well known in the art to implant devices such as replacement heart valves, clips, stents, and reinforcement rings, and the like into the human heart to repair the function of the human heart. Similar devices are also introduced into other parts of the human anatomy where mechanical repair is needed. Many such repair operations are carried out by first inserting a delivery catheter by minimally invasive means into a desired organ of the human anatomy. Thereafter, a repair device is passed through an internal lumen along the entire length of the delivery catheter until the repair device reaches the target organ, and the device is pushed out of the distal end of the catheter for implantation. Such devices may expand to assume a new shape once they are pushed out of the delivery catheter, some by means of self-expansion, others by means of mechanical expansion via balloons, expanders, and the like.

One of the problems confronted by such systems known in the art is that the delivery catheter may require to be threaded through a tortuous series of twists and turns through one or more lumens in the patient's anatomy. Once the delivery catheter is in position, the implant device must be pushed up, from outside the patient, through a lumen of this tortuously twisted delivery catheter. If the implant device has a substantial profile in its delivery condition, the surgeon may encounter difficulty in threading the implant device around all the tight corners of the delivery catheter. Further, once the implant device reaches the distal end of the delivery catheter, the surgeon may find that she has no control over the orientation of the distal end of the catheter because the catheter has effectively neither tortional stiffness, nor longitudinal stiffness extending unbroken all the way from the proximal end where a control handle is located, to the distal end where the device will eventually be delivered. Although delivery catheters may include pullwires to facilitate positioning the catheter's distal tip in a three dimensional space, such pullwire systems are frequently difficult to operate and not reliable for exact positioning.

Therefore there exists a need in the art for improved systems and methods for delivering implant devices to a distal end of a delivery catheter, and once having so delivered, to be able to manipulate the distal end of the catheter by manipulating the proximal end of the catheter. The present invention addresses these and other needs.

SUMMARY OF THE INVENTION

In one embodiment, the invention is a method of delivering an implant into a heart of a patient, the heart having a left atrium and a right atrium. The method comprises creating an entryway into the anatomy of a patient via a femoral artery. Then a trans-septal puncture is performed between the right atrium and the left atrium. A catheter is inserted into the patient via the femoral artery. The catheter has a proximal end communicating via a bore to a distal end. The catheter has a first joint, and a second joint that is located distal of the first joint, wherein, the first joint and the second joint are separated by a first digit that is rotationally rigid at all points between the first joint and the second joint, and further wherein the second joint and the distal end are separated by a second digit that is rotationally rigid at all points between the second joint and the distal end. The catheter is advanced into the patient until the first joint and the distal end are located in the right atrium and an implant is located, within the bore, distal of the first joint. The first joint is bent. The distal end is passed via the trans-septal puncture into the left atrium until the second joint is located in the left atrium. The implant is moved within the catheter until the implant is located distal of the second joint. One of ordinary skill will appreciate that securing an implant at a location adjacent the distal end of a delivery catheter, inside the left atrium, without having been obliged to push the implant around a number of tortuous bends inside a catheter, is a highly advantageous outcome.

In some embodiments, the method further includes bending the second joint; and thereafter, it may include manipulating a position of the implant in relation to the heart by rotating the proximal end of the catheter about an elongate axis of the catheter. One of ordinary skill will appreciate that the ability to position the implant in relation to the heart by rotating the proximal end of the catheter is not feasible in current catheters because the current catheters are not tortionally rigid enough between distal end and proximal end to permit such control from the proximal end. Once the implant is positioned at a desirable location, the method may include ejecting the implant from the bore at the distal end, and this may include ejecting the implant towards a mitral valve of the heart. In some embodiments, performing a trans-septal puncture includes routing a guidewire from the femoral artery into the left atrium, and advancing the catheter may include passing the catheter over the guidewire. In some embodiments, bending the first joint may include manipulating pullwires passing through the catheter; and it may also include bending a first joint that is an articulated joint, which in turn may include rotating the articulated joint about a pin connector.

In another embodiment, the invention may be a catheter for delivering an implant to a desired location within a patient. In some embodiments, the catheter comprises a shaft having a proximal end and a distal end and a bore extending between the proximal end and the distal end. It may also include a first joint in the shaft, the first joint being configured to permit adjacent portions of the shaft to rotate in relation to each other within a single plane. It also includes a second joint in the shaft located distal of the first joint, the second joint being configured to permit adjacent portions of the shaft to rotate in relation to each other within a single plane. Under this configuration, the first joint and the second joint are separated by a first digit that is rotationally rigid at all points between the first joint and the second joint. Furthermore, the second joint and the distal end are separated by a second digit that is rotationally rigid at all points between the second joint and the distal end. Again, under this configuration, the first digit and the second digit, taken together, are sized to receive an implant entirely within the bore between the first joint and the distal end.

In some embodiments, the first digit is sized to receive an implant entirely within the bore between the first joint and the second joint. In other embodiments, the second digit is sized to receive an implant entirely within the bore between the second joint and the distal end.

In further embodiments, the second digit includes a conical portion that is flexible in a radial direction. This aspect permits an implant to be forced distally into and through the conical portion, while the conical portion can expand radially to permit passage of the implant. In yet further embodiments, the first joint is an articulating joint, and the articulating joint may include a pin. In further embodiments, the first joint and the second joint are the only joints in the shaft between the proximal end and the distal end. One of ordinary skill will appreciate that by reducing the number of joints, a catheter is formed that has a high degree of torsional rigidity, and permits an operator to rely on that rigidity to position an implant at the distal end, while manipulating the catheter from the proximal end which extends outside the patient.

These and other advantages will become apparent when read in conjunction with the drawings and the detailed description of embodiments.

DETAILED DESCRIPTION OF THE EMBODIMENTS

As may be understood from this detailed description, as read in conjunction with the figures, a catheter having features of the invention is described. The context of the invention is explained with initial reference to FIGS. 1-5.

Figure 1:
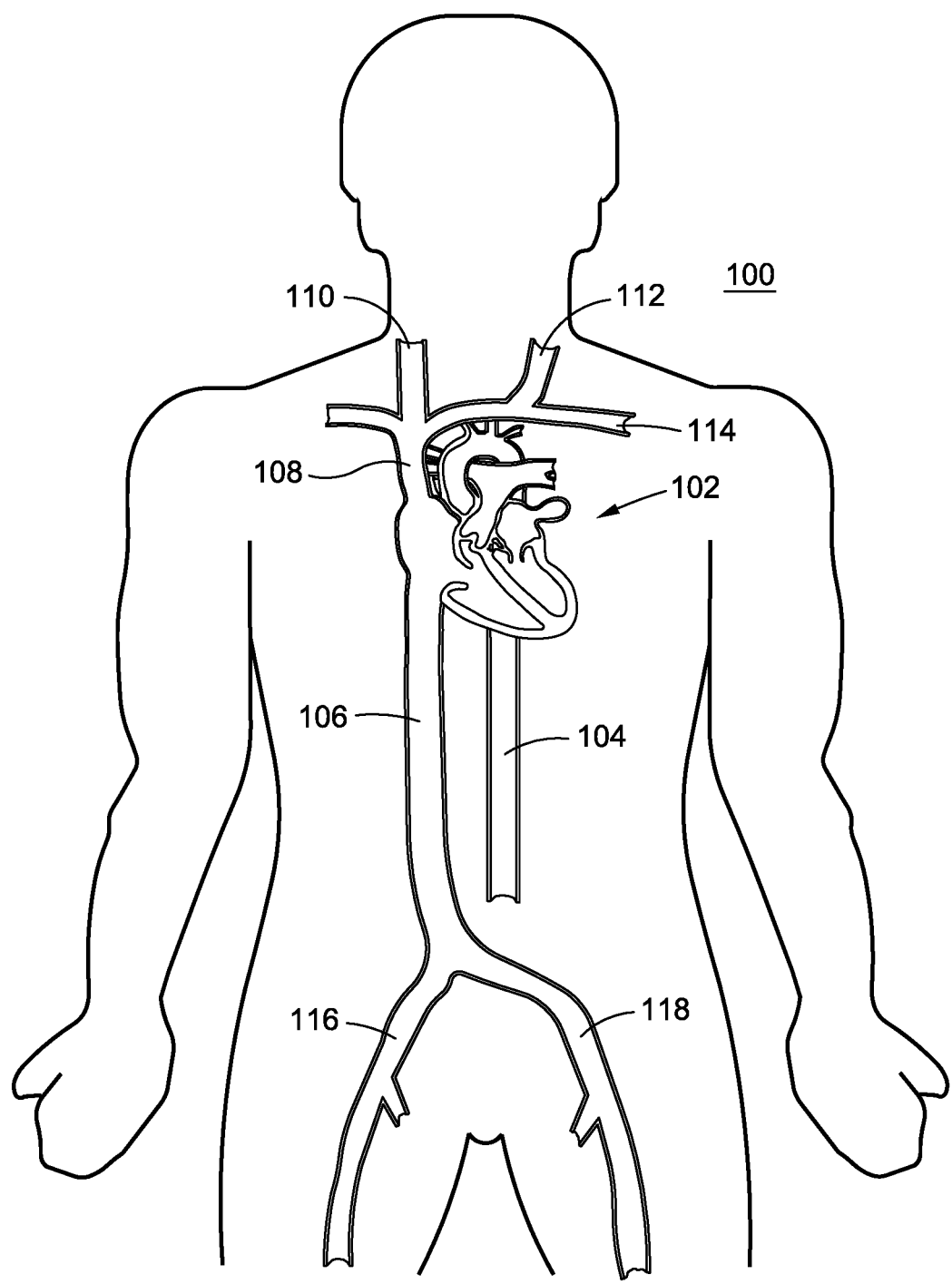
FIG. 1 is a front view schematic representation of the human venous circulatory system including the heart and the great veins.

Referring to FIG. 1, there is shown a schematic frontal illustration, looking posteriorly from the anterior side of the patient 100. The heart 102 is a pump, the outlet of which is the aorta, including the descending aorta 104, which is a primary artery in the systemic circulation. The circulatory system, which is connected to the heart 102 further comprises the return, or venous, circulation. The venous circulation comprises the superior vena cava 108 and the inferior vena cava 106. The right and left jugular veins, 110 and 112, respectively, and the subclavian vein 114 are smaller venous vessels with venous blood returning to the superior vena cava 108. The right and left femoral veins, 116 and 118 respectively, return blood from the legs to the inferior vena cava 106. The veins carry blood from the tissues of the body back to the right heart, which then pumps the blood through the lungs and back into the left heart. The arteries of the circulatory system carry oxygenated blood (not shown) from left ventricle of the heart 102 to the tissues of the body.

Figure 2:
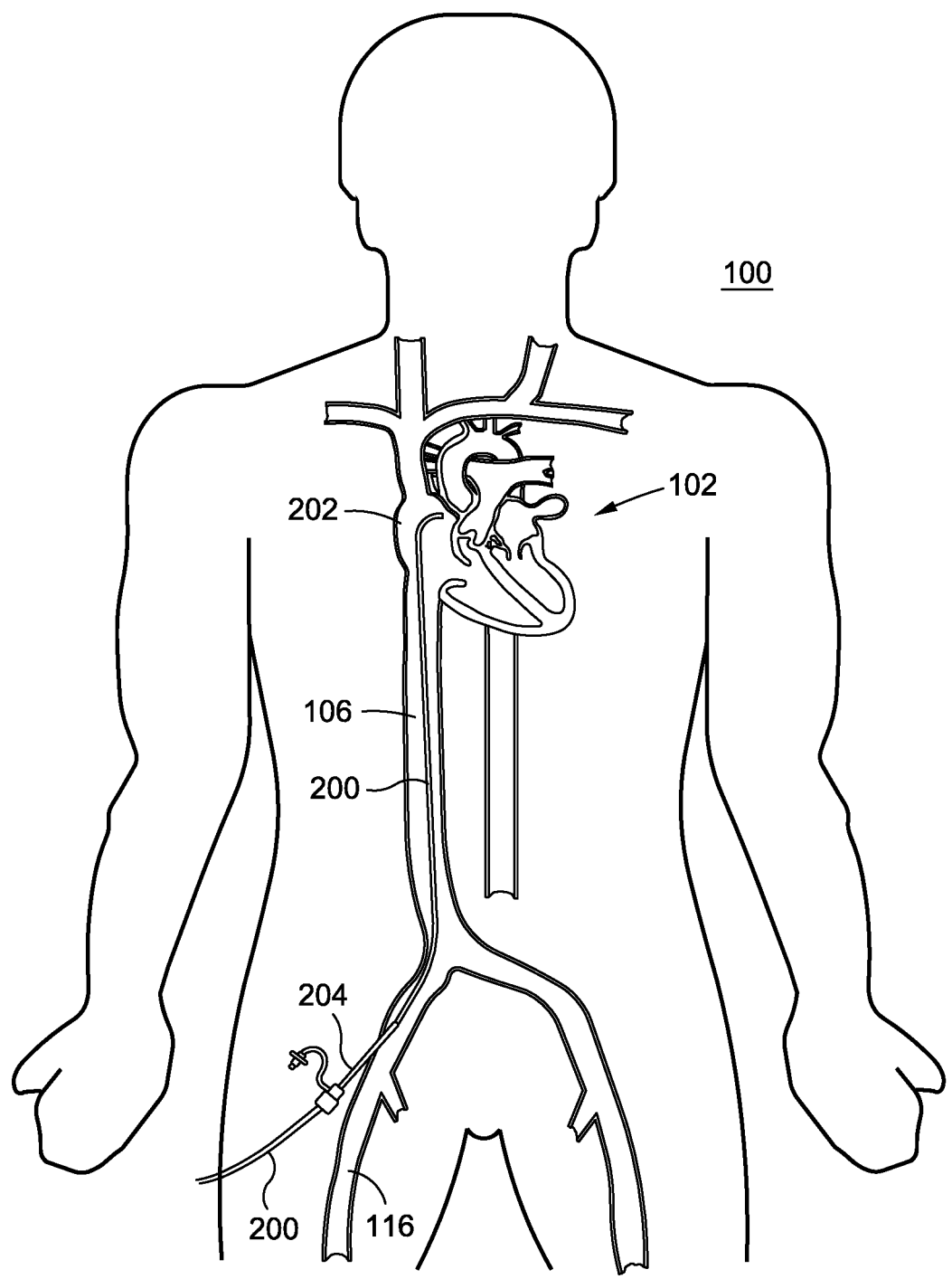
FIG. 2 is a front view schematic representation of the human venous circulatory system with a guidewire routed from the femoral vein into the right atrium.

FIG. 2 (prior art) shows that a vascular introduction sheath 204 has been inserted into the right femoral vein 116 via a percutaneous puncture or incision. A guidewire 200 has been inserted through the introduction sheath 204 and routed up the inferior vena cava 106 to the right atrium 202, one of the chambers of the heart 102. In this illustration, the left anatomical side of the patient 100 is toward the right. The guidewire 200 has been placed so that it can be used to track a delivery catheter into a region of the heart 102.

Figure 3:
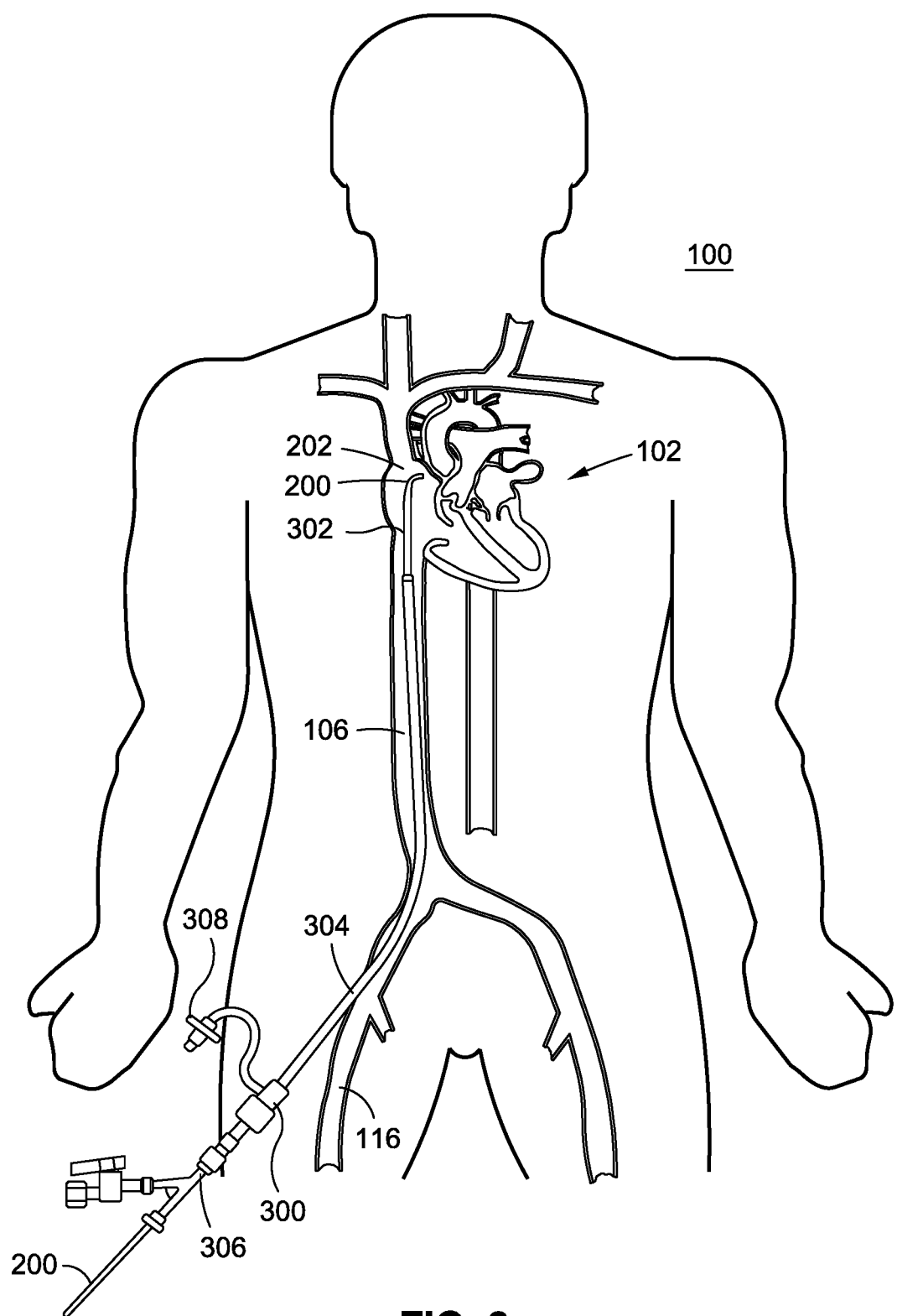
FIG. 3 is a front view schematic representation of the human venous circulatory system with an expandable sheath advanced into the right atrium.

FIG. 3 (prior art), is a frontal illustration, looking posteriorly from the anterior side, of the patient 100. The vascular introduction sheath 204 of FIG. 2 has been removed from the right femoral vein 116 and a larger trans-septal expandable sheath 300 has been inserted into the venous circulation over the guidewire 200 and routed through the inferior vena cava 106 into the right atrium 202 of the heart 102. The expandable trans-septal sheath 300 further comprises a dilator 306, the proximal most part of which is shown in FIG. 3. The expandable trans-septal sheath 300 further comprises a proximal non-expandable region 304 and a distal expandable region 302.

Figure 4:
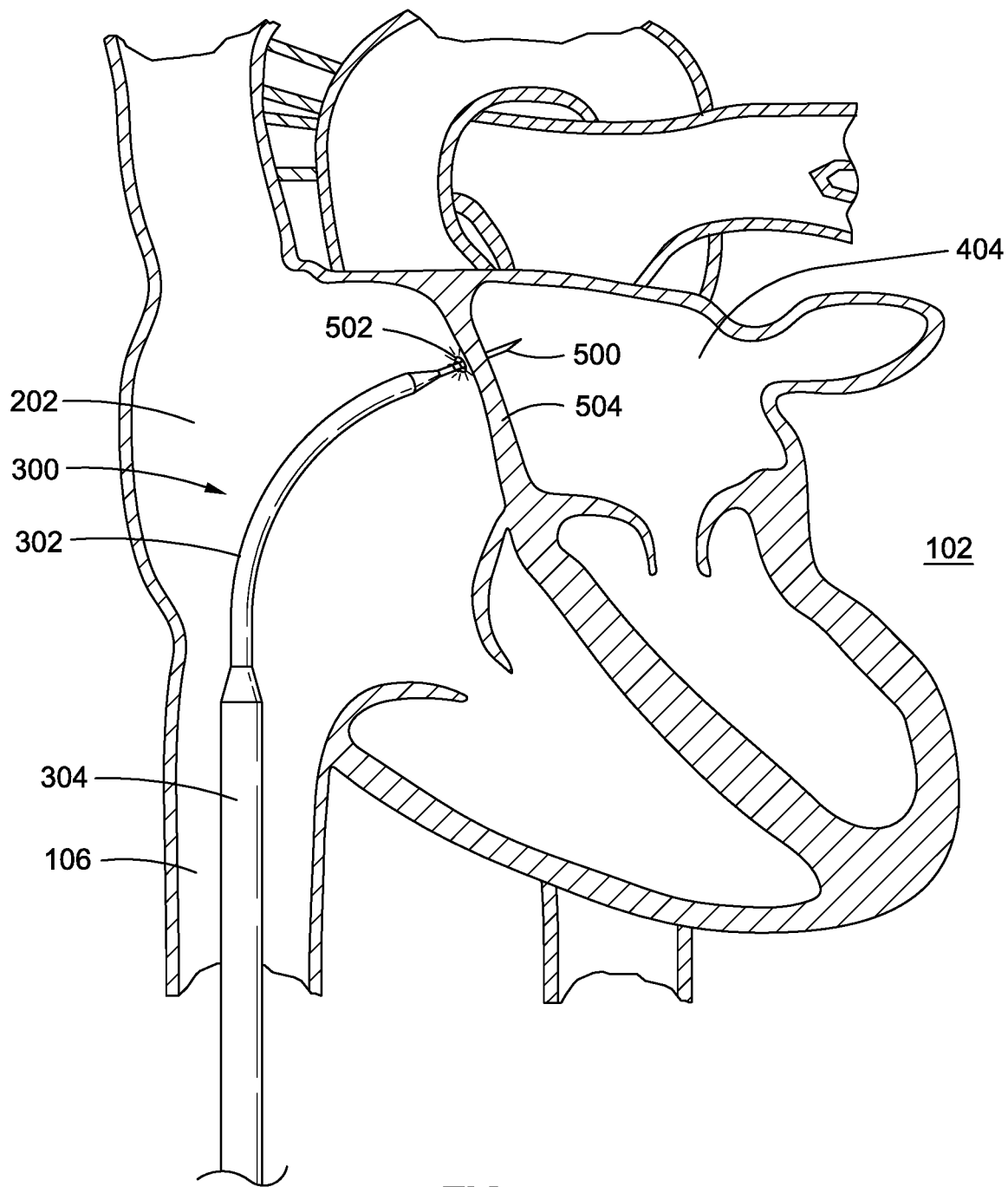
FIG. 4 is a cross-sectional illustration of the heart with the expandable sheath positioned at the atrial septum and the septal penetrator advanced across the atrial septum into the left atrium, according to an embodiment of the invention.

FIG. 4 (prior art), is a cross-sectional illustration of the heart 102, showing the atrial septum 504. The distal expandable region 302 of the sheath 300, substantially located within the right atrium 202, is shown with its long axis perpendicular to the atrial septum 504, The proximal end 304 of the sheath 300 is shown resident within the inferior vena cava 106. A septal penetrator 500 is shown extended through a puncture 502 in the atrial septum 504 and is routed into the left atrium 404. The septal penetrator 500 is a needle or axially elongate structure with a sharp, pointed distal end. The septal penetrator 500 is actuated at the proximal end of the sheath 300. The septal penetrator 500 is operably connected to a control mechanism such as a button, lever, handle, trigger, etc., which is affixed, permanently or removably, at the proximal end of the dilator 306 by way of a linkage, pusher rod, or the like that runs the length of the dilator 306.

Figure 5:
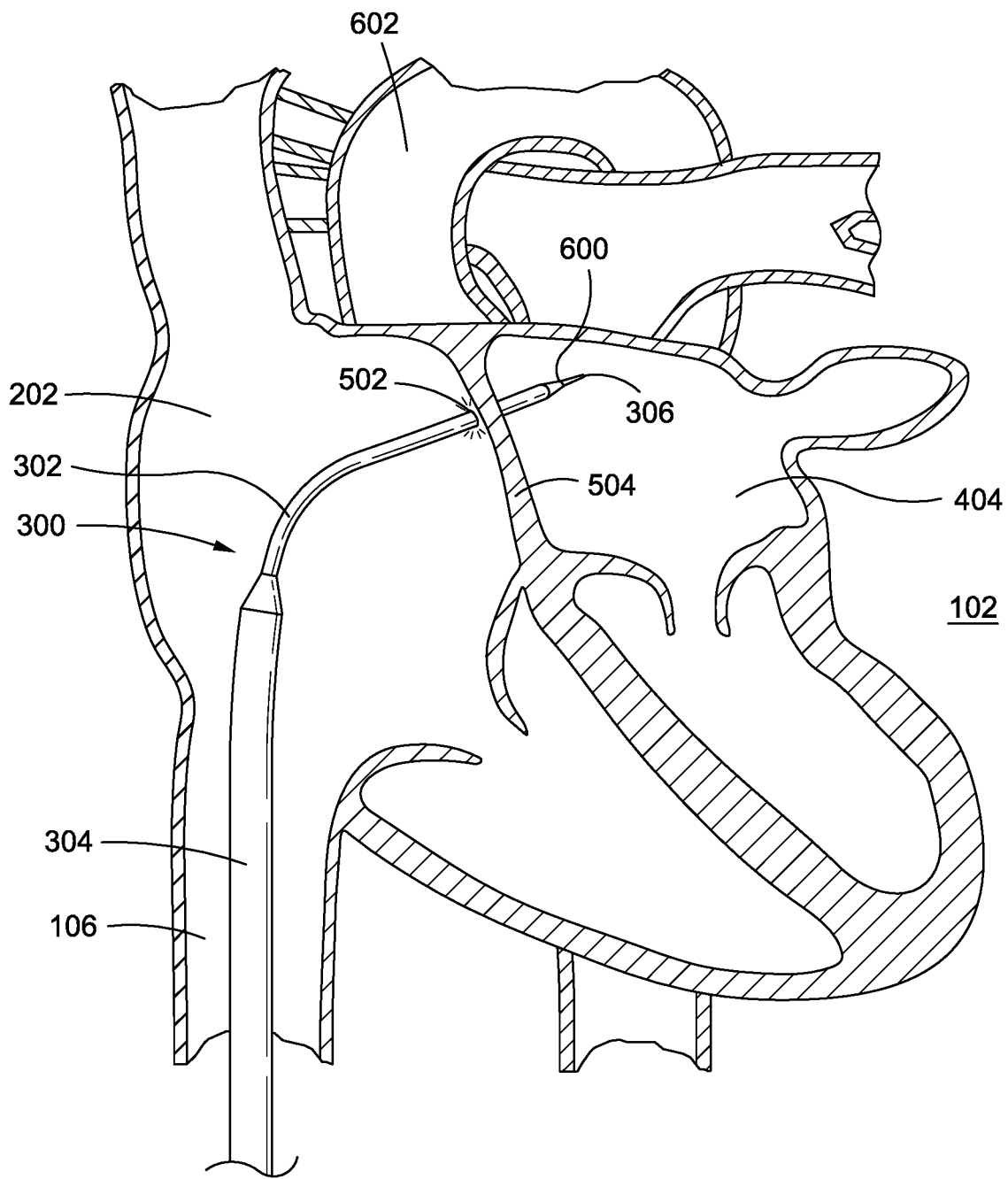
FIG. 5 is a cross-sectional illustration of the heart with the expandable sheath advanced into the left atrium across the atrial septum and the septal penetrator withdrawn into the dilator of the expandable sheath, according to an embodiment of the invention.

FIG. 5 (prior art), illustrates a cross-sectional view of the heart 102 showing the distal expandable region 302 having been advanced across the atrial septum 504 from the right atrium 202 and into the left atrium 404. The tapered tip 600 of the dilator 306 leads the distal end of the expandable region 302 through the septal puncture 502 created by the penetrator 500.

Once the puncture 502 is successfully formed in the septum 504, a guidewire 200 is redirected down the catheter 300 to extend into the left atrium 404, and the catheter 304 is removed from the patient's anatomy, while leaving the guidewire 200 in position. The foregoing is a method known in the art for placing a guidewire across a puncture in the septum, as exemplified in U.S. Publication 20060135962, incorporated herein in its entirety.

Figure 6A:
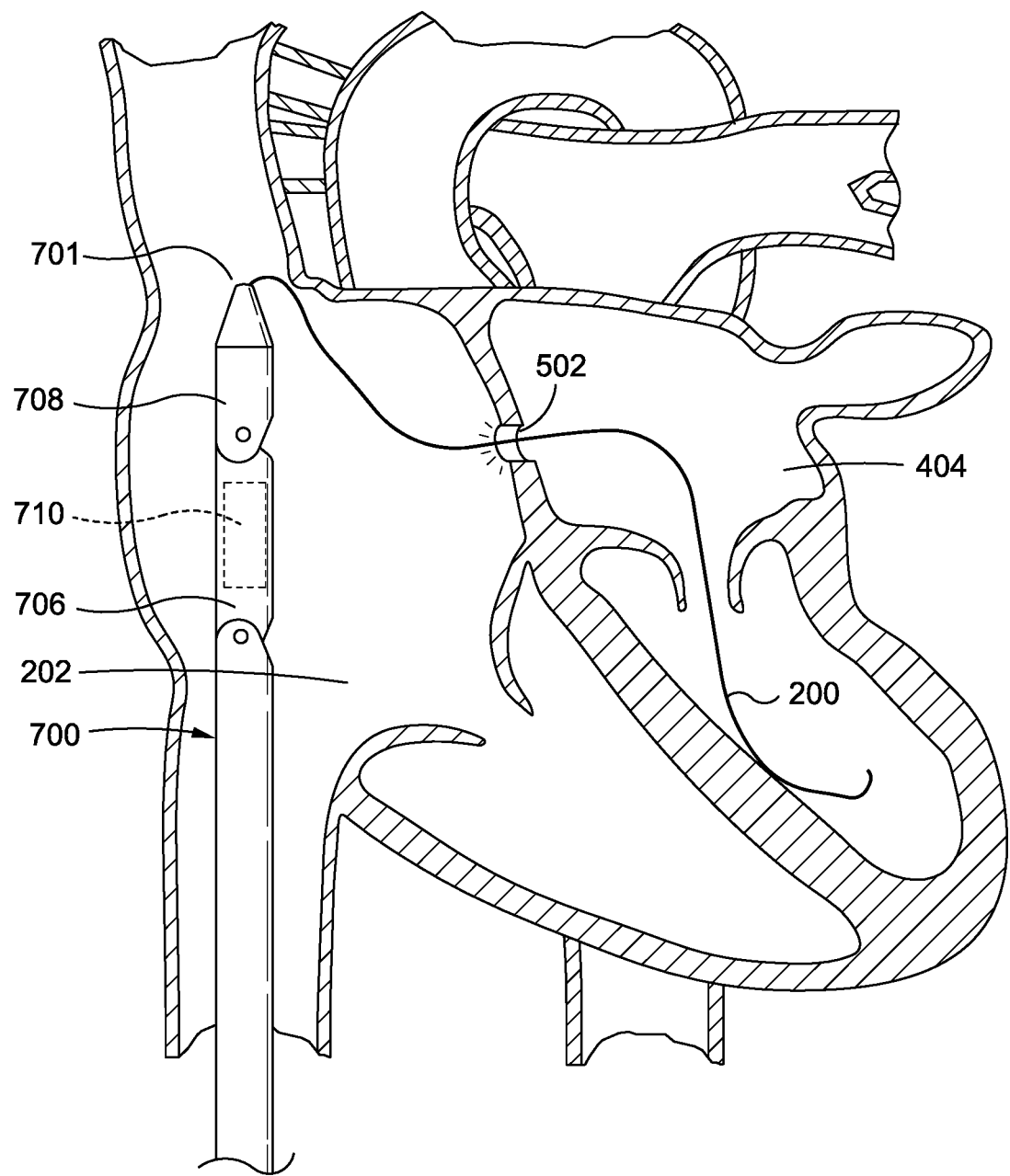
FIG. 6A is a cross-sectional illustration of the heart with a novel catheter advanced into the right atrium according to an embodiment of the invention.
Figure 6B:
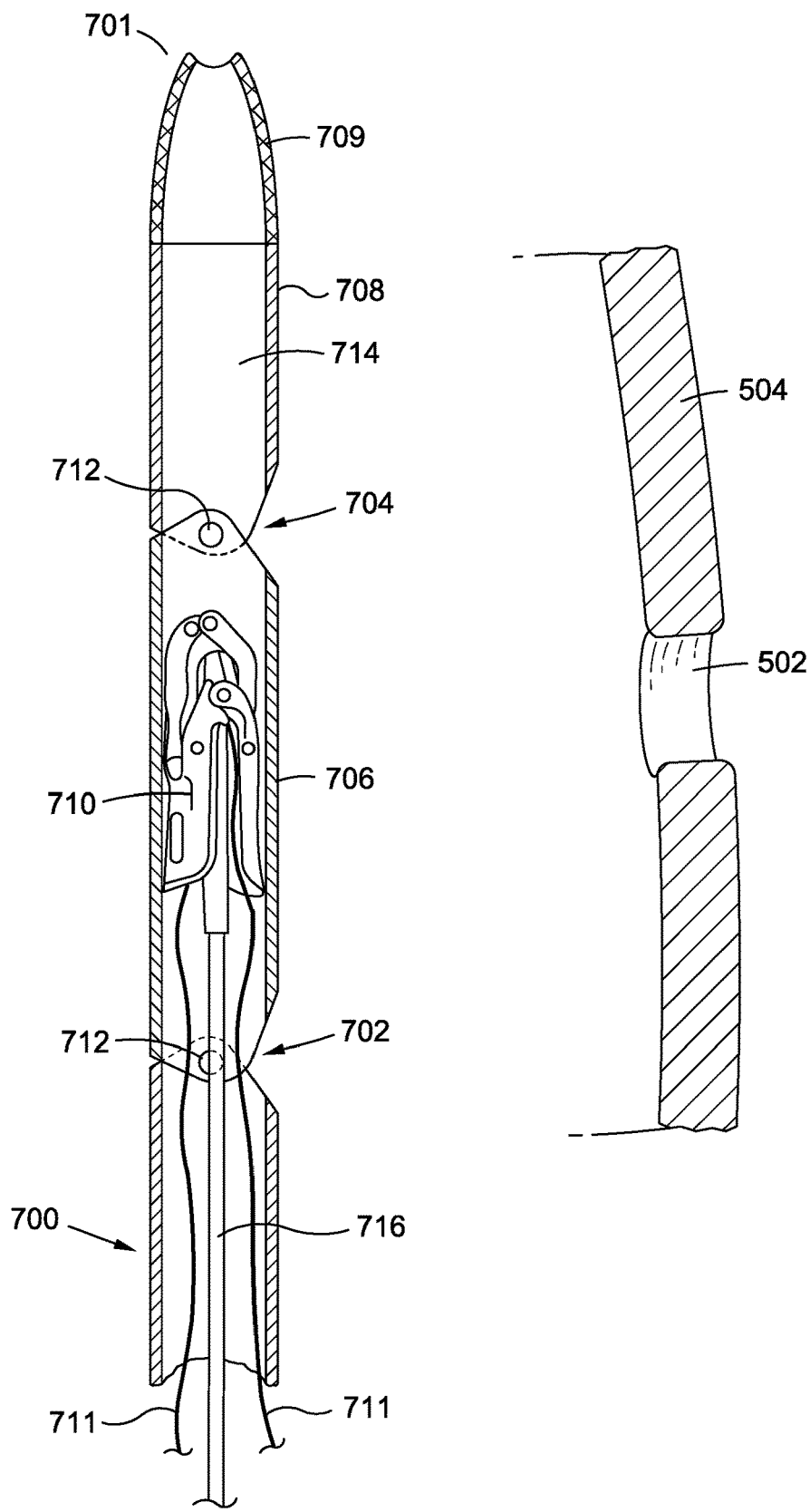
FIG. 6B is a cross-sectional illustration of the novel catheter seen in FIG. 6A.

At this point a novel catheter 700 according to embodiments of the present invention is described starting with reference to FIG. 6A and FIG. 6B. The catheter 700 is introduced over the guidewire 200 until the distal end 701 of the catheter protrudes into the right atrium 202.

Before proceeding to describe an embodiment of a novel method for delivering an implant once the septum 504 has been punctured, a novel catheter is described here that is suitable for carrying out embodiments of the invention. With reference to FIG. 6A and FIG. 6B, the catheter 700 of the present invention is designed and configured to provide the surgeon user with a delivery instrument for advancing a relatively inflexible implant device 710 to a desired location in the human anatomy. The invention is not limited by the type of implant device, and this may take the form of a heart valve, a clip, a stent, a reinforcement ring, or similar.

It will be understood by one of ordinary skill, and with reference to FIG. 3 that the shape assumed by the catheter 700, as it is extended from the femoral artery at the proximal end all the way to the right atrium 202, follows a profile that is substantially a straight or linear configuration. As will be described, it is only at the very distal end of its travel that the shape of the catheter 700 will be required to depart from a substantially straight configuration for its proper use.

In order to provide this characteristic, the catheter 700 is fabricated so that it is substantially stiff all the way along its length from its proximal end to near its distal end, and is at least stiff enough to receive a distally directed force exerted by the user without buckling. However, at its distal end the catheter is provided with two specific points of articulation, a first point of articulation at a proximal joint 702 and a second point of articulation at a distal joint 704.

FIG. 6B exemplifies the structure of a joint that will be suitable to accomplish the objective of this embodiment of the invention. Each joint is configured to make a sharp turn, and in some embodiments the joints are configured to articulate about a pin 712. In other embodiments, the joint may be configured to articulate about a ball and socket joint, or other known system or articulation. Such joints are described more fully in application Ser. No. 13/675,934, which is incorporated herein in its entirety.

Figure 7A:
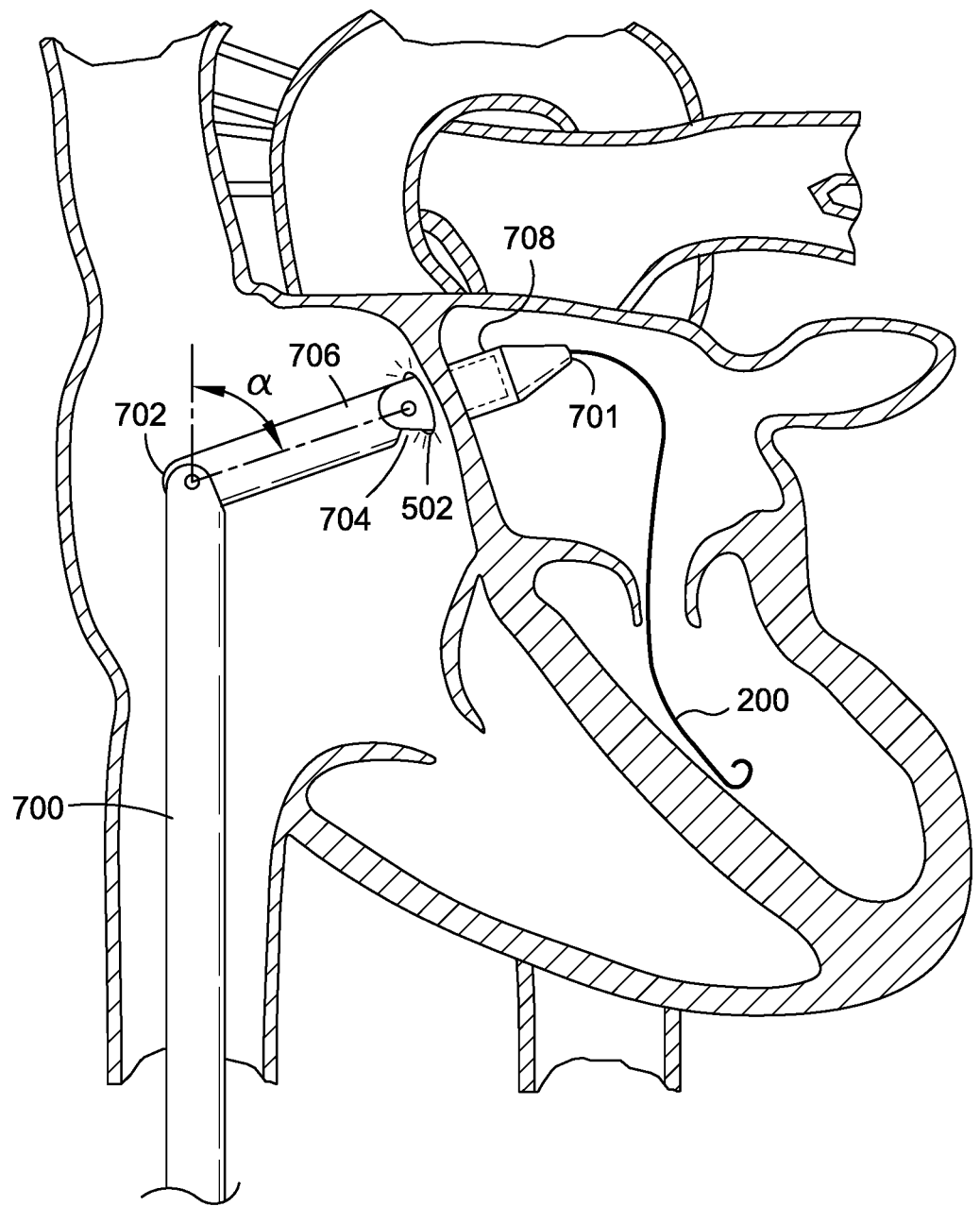
FIG. 7A is a cross-sectional illustration of the heart with the catheter of FIGS. 6A and 6B advanced into the right atrium according to an embodiment of the invention.
Figure 7B:
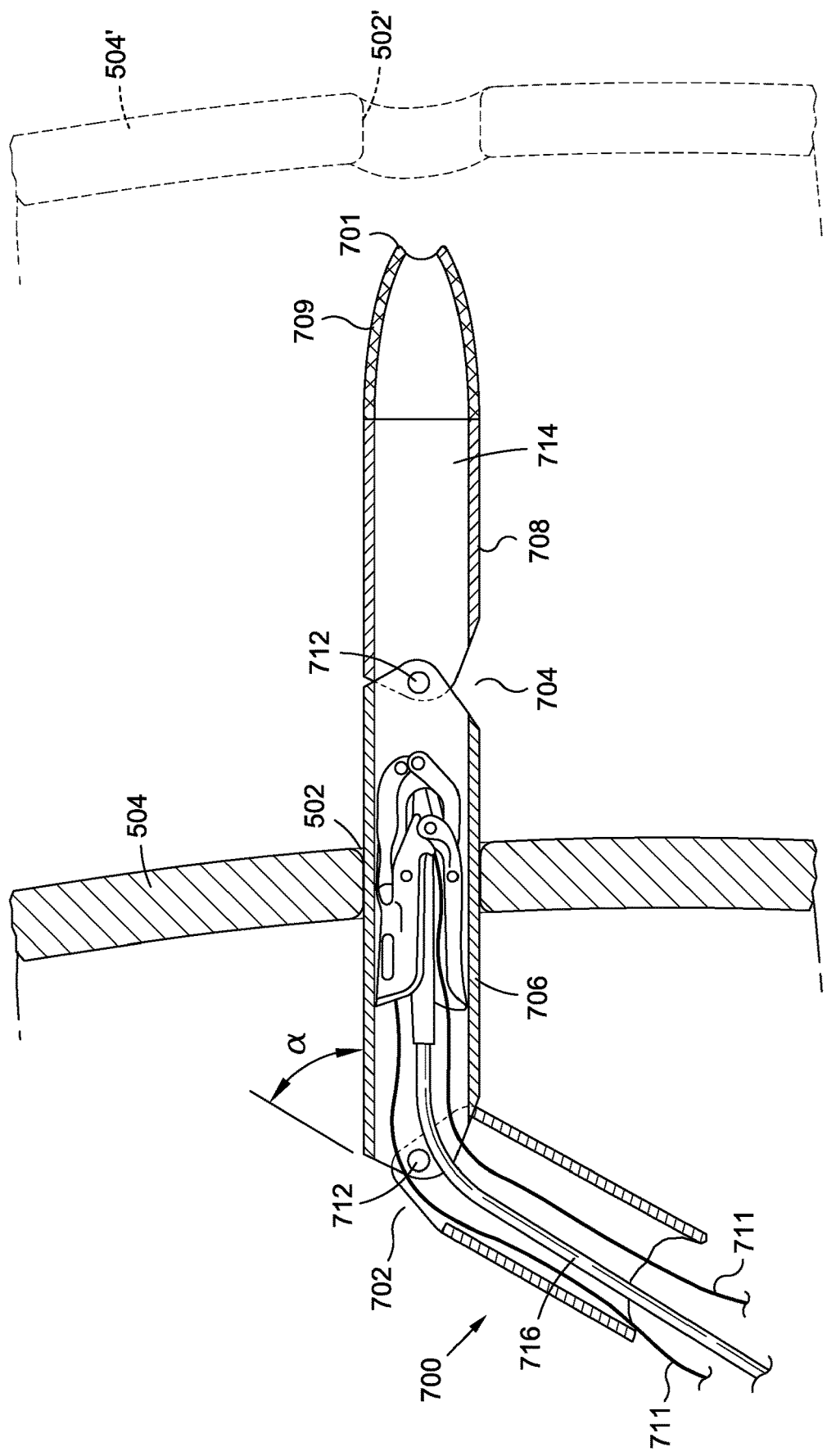
FIG. 7B is a cross-sectional illustration of the novel catheter in the configuration seen in FIG. 7A.

In some embodiments, the joints 702, 704 described are configured to bend away from a straight configuration in only one plane, and then to stop bending when a limit of travel has been reached. For example, FIGS. 7A and 7B show that the first joint 702 has been bent through an angle α which allows the distal end 701 of the catheter to be extended through the puncture 502 that has been made in the septal wall 504 as described herein. Both first joint 702 and second joint 704 are configured so that after a limited angle of bending has been travelled, the joint can bend no further, and is effectively "locked" against further movement. The movement of the joint into a bent condition is effected by pullwires (which, for sake of clarity, are not shown in the figures) that are positioned to extend axially along the circumference of the catheter according to known technology such as that described in application Ser. No. 13/675,934, and incorporated herein.

The section of the catheter that lies between the first joint 702 and the second joint 704 is referred to herein as the proximal digit 706 (or first digit) and the section that extends between the second joint 704 and the distal end 701 as the distal digit 708 (or second digit). In some embodiments, these digits are rigid and are configured to not possess additional joints within the length of each one of them. These qualities in the digits 706, 708 are referred to herein as being "rotationally rigid." Therefore, when the first joint 702 and second joint 704 are the only joints in the catheter, and when they are locked into a bent configuration by forces exerted through pullwires, they are configured to faithfully transmit any movement (rotational or translational) of the proximal end of the catheter to the distal end 701 thereof. At the distal end of the distal digit 708, a flexible cone 709 may be affixed. This cone provides a narrowed and pointed end that facilitates passing the distal end 701 of the catheter through the septal puncture 502 and may be fabricated from a suitable flexible polymer. The cone is radially flexible in order to permit an implant 710 to be pushed out of the distal end of the bore 714 that extends through the catheter. The cone will be expanded by the implant as it is forced distally through the cone.

In use, the invention is applied as follows. A desired implant 710 is inserted into the bore 714 of the catheter, and is advanced distally until it is positioned inside the proximal digit 706 so that it is positioned entirely between the first joint 702 and the second joint 704 as seen in FIG. 6B. The implant may be a clip designed to repair a mitral valve (as is exemplified in FIG. 6B) or it may be a prosthetic mitral valve, or other implant type device known in the art for repairing body organs. A flexible push rod 716 is attached to the proximal end of the implant 710 and extends down the bore 714 of the catheter to the proximal end of the catheter. The push rod is suitable for developing sufficient column strength to push the implant distally and to control the deployment of the implant 710 once it has been ejected from the catheter according to known means. Control wires 711 may be attached to the implant to control the implant during and after deployment.

The catheter 700 is then advanced over the guidewire 200 from the femoral artery at the proximal end, all the way to the right atrium 202, as may be envisaged by reference to FIGS. 6A and 6B. It will be appreciated that in the case where an implant occupies the center of the catheter bore 714 (such as exemplified in FIG. 6B), it may not be feasible to insert a guidewire down the center of the bore 714. However, it is well known to provide a lumen for receiving a guidewire that extends along the circumferential wall of the catheter, and such a lumen will be provided in a case where the center of the catheter bore is blocked by an implant. For the sake of clarity such a lumen for a guidewire located on the circumferential wall of the catheter is not shown in the figures, but may be envisaged by reference to U.S. Pat. No. 8,317,715 which is incorporated herein in its entirety.

At this point in the process, the first joint 702 may be bent by using the pullwires (not shown) so that the distal tip 701 of the catheter faces the puncture 502' in the septal wall 504'. The septal wall and puncture 502' are shown in dotted in FIG. 7B, and the distal tip 701 of the catheter is lined up with the puncture with the aid of the guidewire. Then, the distal tip 701 may be pushed through the puncture 502 as is exemplified in FIG. 7B in solid line, until the second joint 704 enters the left atrium when passed through the puncture 502 as exemplified in FIG. 7B.

Figure 8:
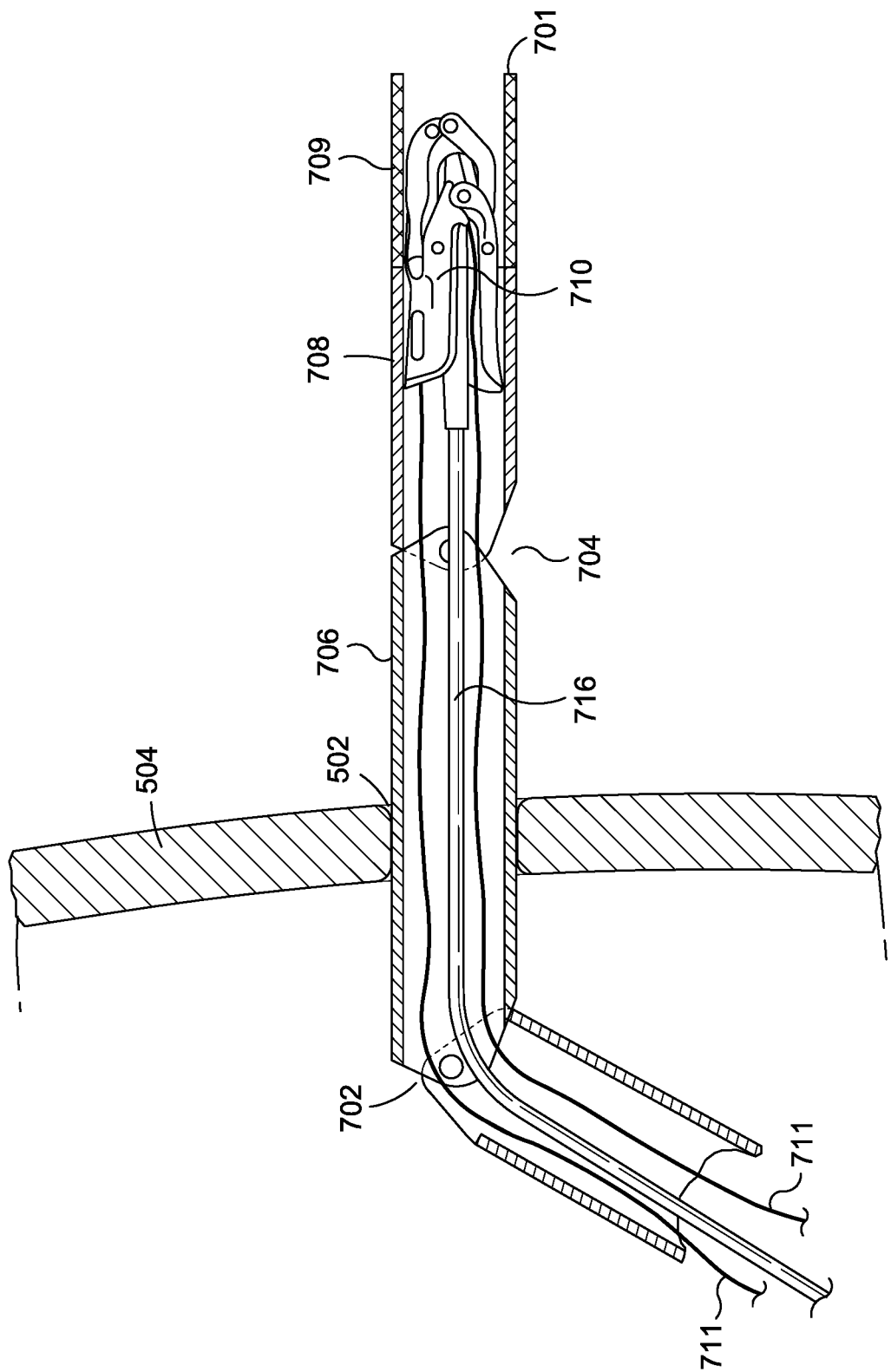
FIG. 8 is a cross-sectional illustration of the novel catheter in a further bent configuration according to an embodiment of the invention.

At this point in the process, the implant 710 may be pushed distally within the bore 714 of the catheter using the flexible push rod 716 until it is entirely located in the distal digit 708, distally of the second joint 704, as exemplified in FIG. 8. It will be appreciated that under this configuration, the flexible cone 709 is forced to expand radially outwardly, losing its conical shape to accommodate the implant 710.

Figure 9A:
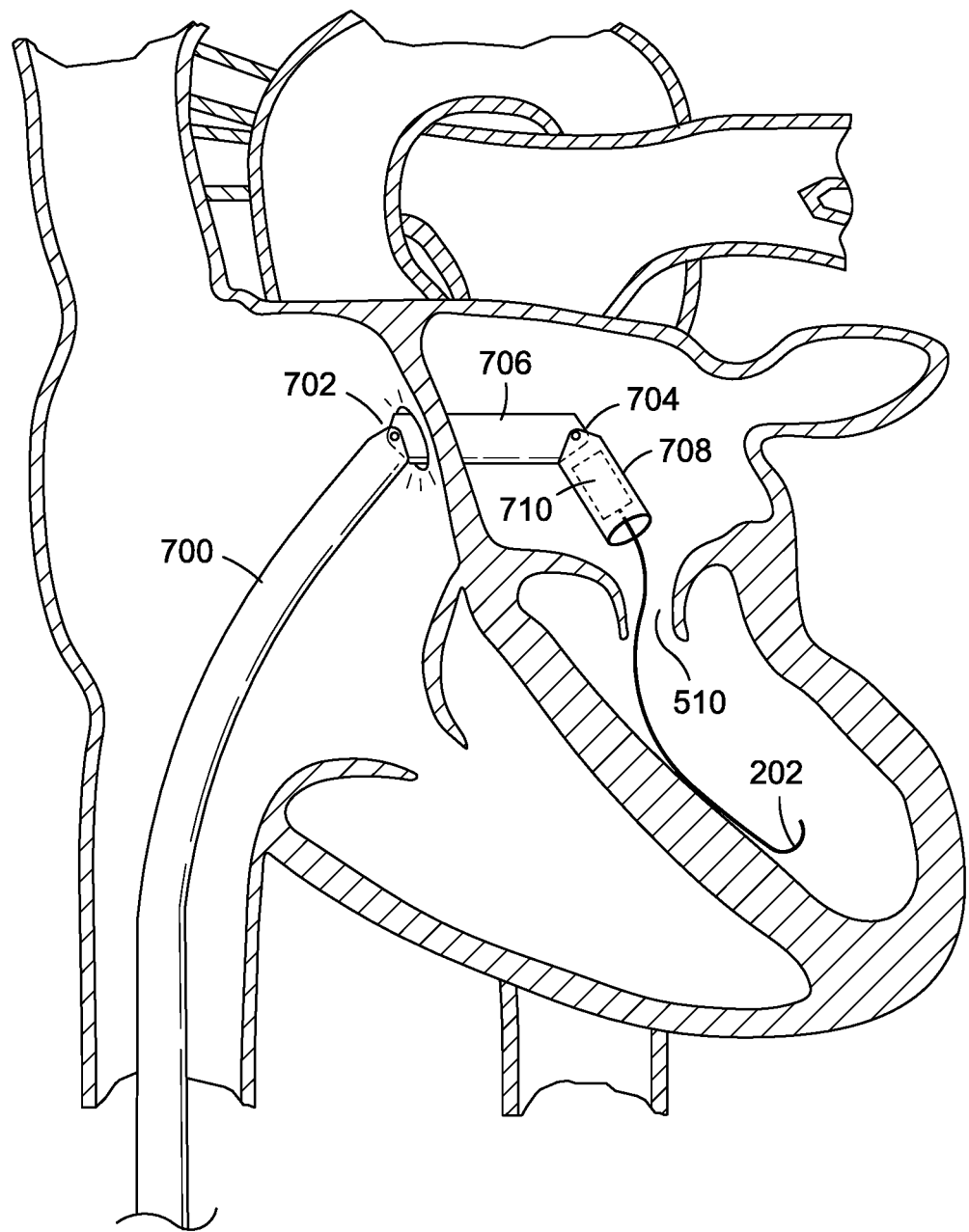
FIG. 9A is a cross-sectional illustration of the heart with the catheter of FIGS. 6A and 6B advanced into the right atrium and bent according to an embodiment of the invention.
Figure 9B:
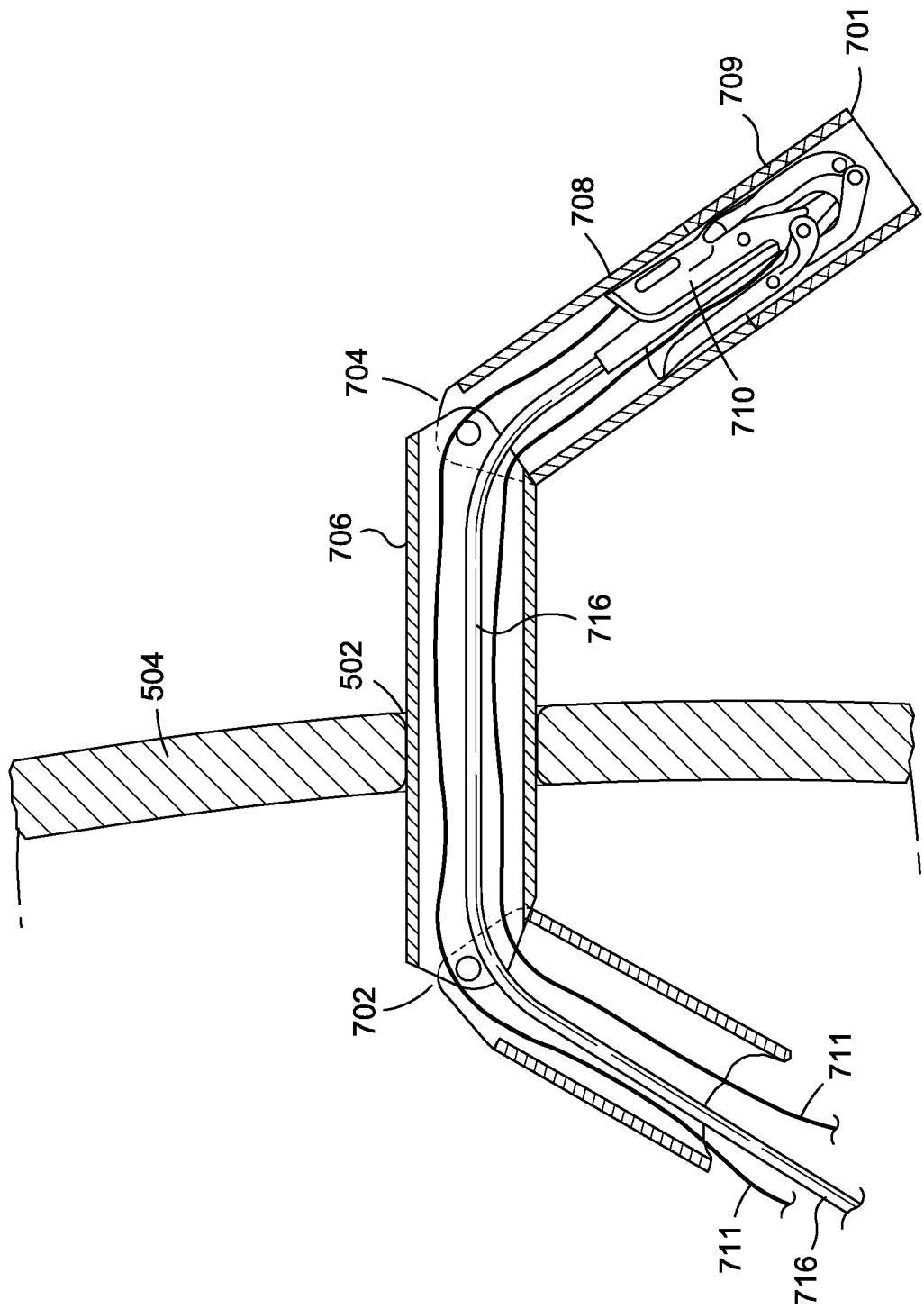
FIG. 9B is a cross-sectional illustration of the novel catheter in the configuration seen in FIG. 9A.

Then, when this step is complete, the second joint 704 may be bent using the pullwire system (not shown) so that the distal digit 708 points downward toward the mitral valve 510, as exemplified in FIGS. 9A and 9B. At this point, the surgeon may manipulate the location of the distal tip 701 of the catheter by using the pullwires controlling the distal joint 704 to move the distal tip laterally (that is, left and right as seen in FIGS. 9A and 9B), and also by rotating the proximal end of the catheter about its elongate axis. Due to the torsional stiffness of the catheter, the distal tip 701 responds to such rotation by moving transversely (that is, in and out of the page as seen in FIGS. 9A and 9B). Thus, the surgeon has the ability to locate the distal tip to any point above the mitral valve 510, ready for the next step.

Figure 10A:
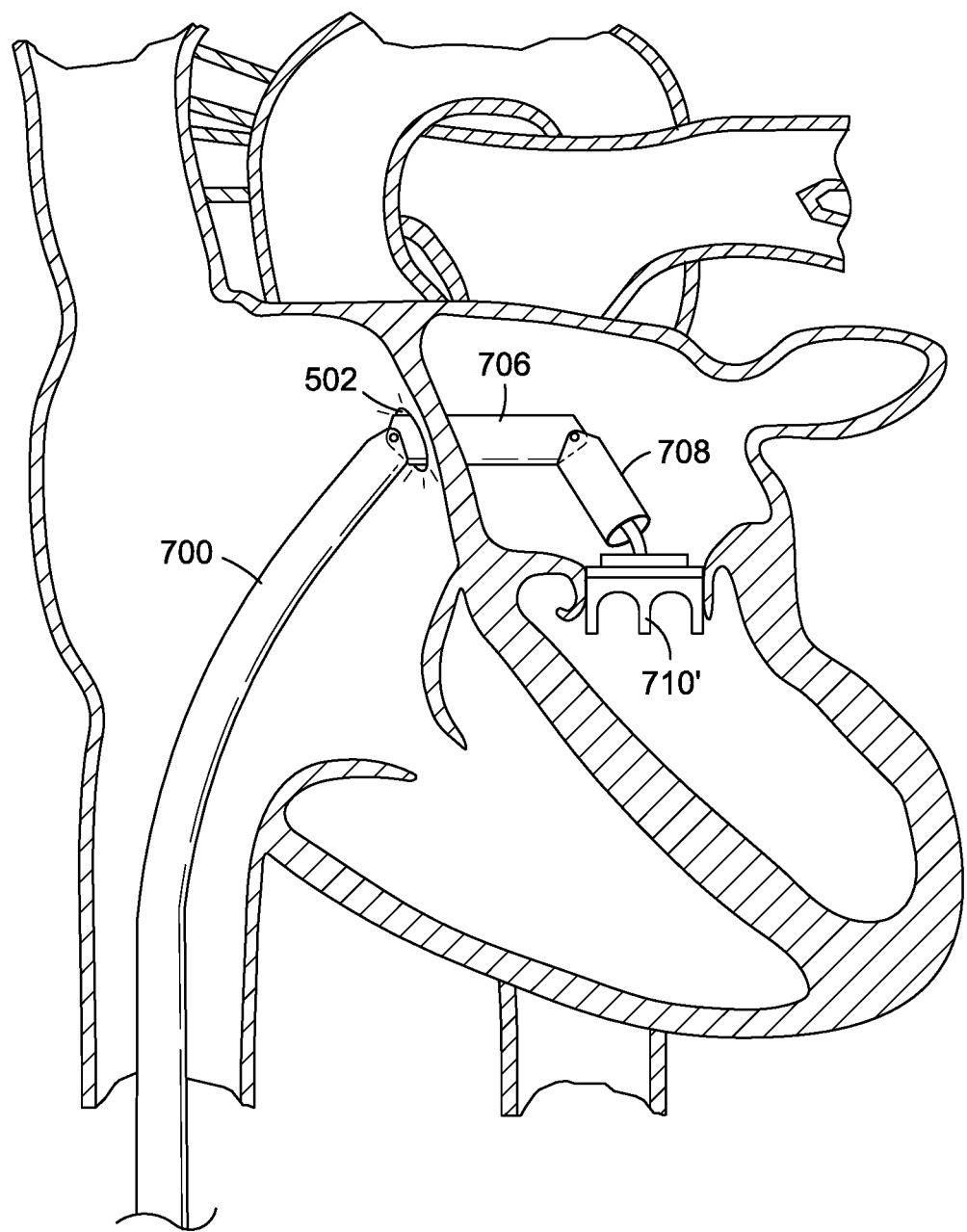
FIG. 10A is a cross-sectional illustration of the heart with the catheter of FIGS. 6A and 6B advanced into the right atrium according to an embodiment of the invention, and delivering a first type of implant.
Figure 10B:
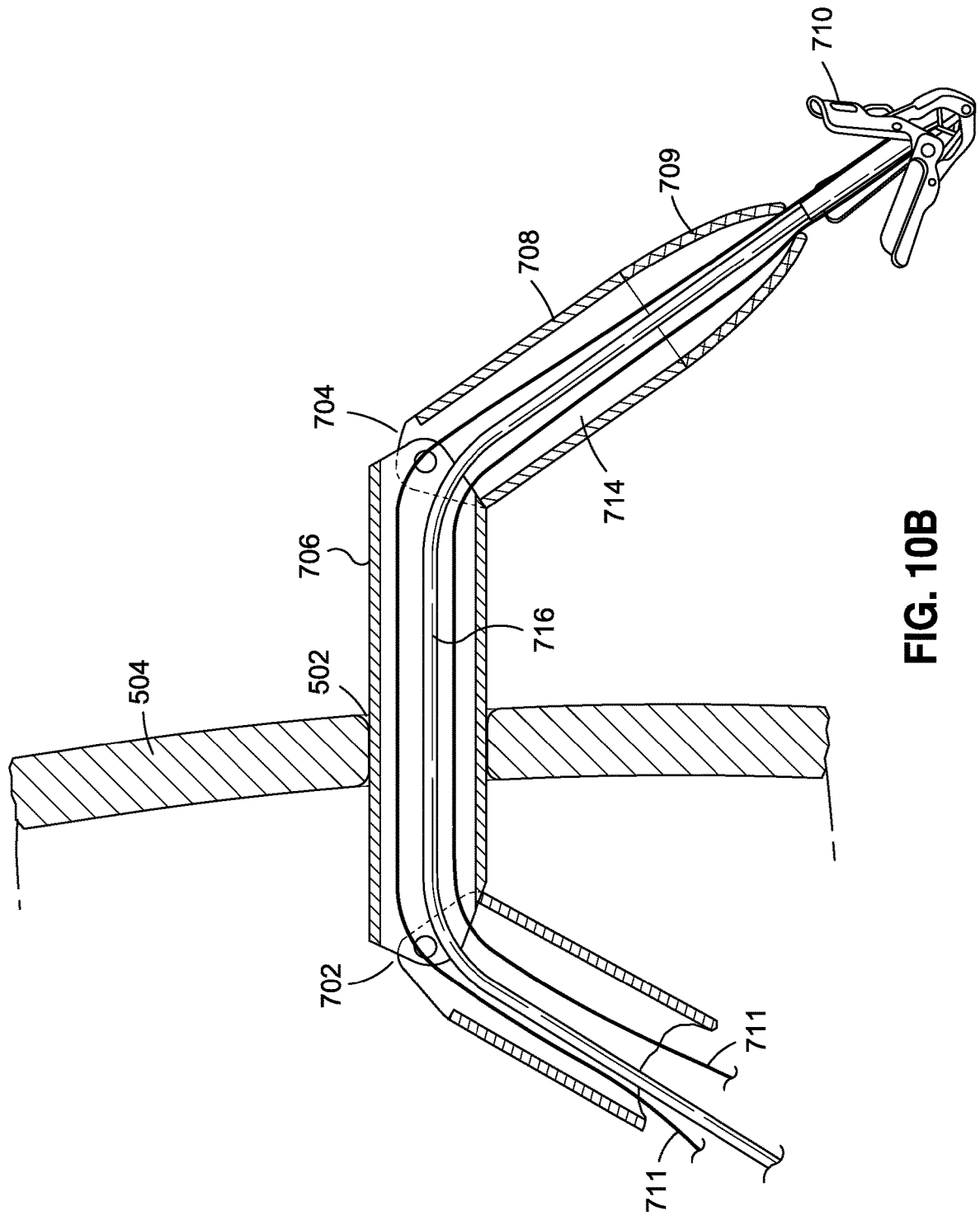
FIG. 10B is a cross-sectional illustration of the novel catheter according to an embodiment of the invention, delivering another type of implant.

During the next step, exemplified in FIG. 10A and FIG. 10B, the implant is pushed out of the bore 714 of the catheter at the distal tip 701. In FIG. 10A, an implant 710' is shown, which, for exemplary purposes, is a prosthetic valve; while in FIG. 10B, an implant 710 is shown which, for exemplary purposes, is a mitral valve clip such as a MitraClip® which is more fully described in U.S. Pat. No. 7,226,467, incorporated herein in its entirety. As noted above, the method of the invention may be carried out using any kind of implant known in the art, and is not limited to implanting valves or clips.

It will be evident to one of ordinary skill in the art that a minimum dimensional requirement of the invention is that the combined length of the proximal digit 706 and the digital digit 708 must be sufficiently long to accommodate the implant 710 entirely within the bore between the first joint 702 and the distal end 701. In some embodiments, it may be desirable for the length of the proximal digit 706 to be sufficient to accommodate the implant 710 entirely between the first joint 712 and the second joint 704. In other embodiments, it may be desirable for the length of the distal digit 708 to be sufficient to accommodate the implant entirely between the second joint 704 and the distal end 701. However, if the implant, once inserted into the bore 714 of the catheter at a location distal to the first joint 702, were to extend across the second joint 704, then the method described above would still be feasible. However, sizing the digits 706, 708 to be large enough to accommodate an implant 710 entirely within a single digit gives the catheter the potential to negotiate a patient's anatomy with greater flexibility in unforeseen circumstances than if the implant extends across the second joint. The configuration chosen for use in a catheter will depend on the type and length of the implant being used, and the nature of human anatomy being targeted for delivery.

Thus, a novel and advantageous system and method for delivering an implant is described that eliminates the need to advance the implant around a tortuous bend in a catheter. Rather, the implant is pushed down a substantially straight bore of the catheter, and any required bending in the catheter takes place only after the implant has been advanced beyond a joint which provides a bend in the catheter. At no point is the inflexible implant required to navigate around a sharp bend in the catheter. This characteristic greatly facilitates the delivery of lengthy and inflexible implants to remote corners of a patient's anatomy.

Although preferred illustrative variations of the present invention are described above, it will be apparent to those skilled in the art that various changes and modifications may be made thereto without departing from the invention. For example, it will be appreciated that combinations of the features of different embodiments may be combined to form another embodiment.

I claim:

1. A system comprising:
an implant having an implant length; and
a catheter, the catheter including
a shaft having a proximal end and a distal end, the shaft defining a bore extending between the proximal end and the distal end;
a first joint in the shaft, the first joint being configured to permit adjacent portions of the shaft to rotate about a first transverse axis in relation to each other within a first single plane; and
a second joint in the shaft located distal of the first joint, the second joint being configured to permit adjacent portions of the shaft to rotate about a second transverse axis in relation to each other within a second single plane;
wherein, the first joint and the second joint are separated by a first digit that is rigid at all points between the first joint and the second joint, the first digit having a first length greater than the implant length; and
the second joint and the distal end are separated by a second digit, the second digit having a second length greater than the implant length.

2. The system of claim 1, wherein the second digit includes a conical portion that is flexible in a radial direction.

3. The system of claim 1, wherein the first joint is an articulating joint.

4. The system of claim 3, wherein the articulating joint includes a pin.

5. The system of claim 1, wherein the second joint is an articulating joint.

6. The system of claim 5, wherein the second joint includes a pin.

7. The system of claim 1, wherein between the proximal end and the distal end, the first joint and the second joint are the only joints in the shaft.

8. The system of claim 1, wherein the second digit is rigid at all points between the second joint and the distal end.

9. A system, comprising:
an implant having an implant length, wherein the implant is one of a mitral valve clip, replacement heart valve, stent, chordal repair implant, annuloplasty implant, leaflet repair implant, or remodeling implant; and
a delivery device having a catheter having
a shaft having a proximal end and a distal end, the shaft defining a bore extending between the proximal end and the distal end,
a first joint in the shaft, the first joint being configured to permit adjacent portions of the shaft to rotate about a first transverse axis in relation to each other within a first single plane; and
a second joint in the shaft located distal of the first joint, the second joint being configured to permit adjacent portions of the shaft to rotate about a second transverse axis in relation to each other within a second single plane;

wherein, the first joint and the second joint are separated by a first digit that is rigid at all points between the first joint and the second joint, the first digit is sized to receive the implant entirely within the bore between the first joint and the second joint, and has a first length greater than the implant length; and the second joint and the distal end are separated by a second digit, the second digit is sized to receive the implant entirely within the bore between the second joint and the distal end, and has a second length greater than the implant length.

10. The system of claim 9, wherein the first plane and the second plane are parallel.

11. The system of claim 9, wherein the second digit includes a conical portion that is flexible in a radial direction.

12. The system of claim 9, wherein the first joint is an articulating joint.

13. The system of claim 12, wherein the articulating joint includes a pin.

14. The system of claim 9, wherein the second joint is an articulating joint.

15. The system of claim 14, wherein the second joint includes a pin.

16. The system of claim 9 wherein, between the proximal end and the distal end, the first joint and the second joint are the only joints in the shaft.

17. The system of claim 9, further comprising a first pullwire configured to effect rotation of the first joint.

18. The system of claim 17, further comprising a second pullwire configured to effect rotation of the second joint.

* * * * *